United States Patent
Mitrovic

(10) Patent No.: US 11,660,169 B2
(45) Date of Patent: May 30, 2023

(54) HYBRID DENTAL IMPLANT AND PRODUCTION METHOD

(71) Applicant: ZM Praezisionsdentaltechnik GmbH, Rostock (DE)

(72) Inventor: Milija Mitrovic, Rostock (DE)

( * ) Notice: Subject to any disclaimer, the term of this patent is extended or adjusted under 35 U.S.C. 154(b) by 547 days.

(21) Appl. No.: 16/663,966

(22) Filed: Oct. 25, 2019

(65) Prior Publication Data

US 2020/0129274 A1    Apr. 30, 2020

(30) Foreign Application Priority Data

Oct. 29, 2018 (DE) ..................... 10 2018 008 528.8

(51) Int. Cl.
- A61C 8/00 (2006.01)
- A61K 6/77 (2020.01)
- A61K 6/802 (2020.01)

(52) U.S. Cl.
CPC .......... *A61C 8/0095* (2013.01); *A61C 8/0066* (2013.01); *A61C 8/0068* (2013.01); *A61C 8/0069* (2013.01); *A61C 8/0089* (2013.01); *A61K 6/77* (2020.01); *A61K 6/802* (2020.01)

(58) Field of Classification Search
CPC ..... A61C 8/0095; A61C 8/006; A61C 8/0068; A61C 8/0069; A61C 8/0089; A61C 8/0045; A61C 8/0066; A61K 6/77; A61K 6/802

See application file for complete search history.

(56) References Cited

U.S. PATENT DOCUMENTS

| | | | |
|---|---|---|---|
| 2004/0234925 A1* | 11/2004 | Benhamou | A61C 8/0063 433/173 |
| 2008/0233538 A1* | 9/2008 | Hug | A61C 8/005 433/174 |
| 2018/0014917 A1* | 1/2018 | Jang | A61C 8/0078 |
| 2019/0247151 A1* | 8/2019 | Bright | A61C 5/30 |

FOREIGN PATENT DOCUMENTS

| | | | |
|---|---|---|---|
| DE | 102011015299 | 9/2012 | |
| DE | 102011015299 A1 * | 9/2012 | ........... A61C 8/0039 |
| EP | 2 039 319 | 3/2009 | |
| EP | 2 688 510 | 1/2014 | |
| EP | 2 742 905 | 6/2014 | |
| EP | 2742905 A1 * | 6/2014 | ........... A61C 8/0012 |
| WO | WO 2012/126447 | 9/2012 | |
| WO | WO-2013075857 A1 * | 5/2013 | ........ B01L 3/502792 |

\* cited by examiner

*Primary Examiner* — Cris L. Rodriguez
*Assistant Examiner* — Drew S Folgmann

(57) ABSTRACT

A dental implant includes an insert element of a titanium-based material inserted and soldered into a blind hole in an anchoring element of a ceramic. The insert element has spacer members to center it in the blind hole, with a uniform circumferential gap space relative to the anchoring element. A portion of the insert element protrudes outwardly beyond an end face of the anchoring element. The blind hole is partly filled with a glass solder, and the insert element is inserted into the blind hole, whereby some of the glass solder is displaced out of the gap space onto the end face of the anchoring element and the protruding portion of the insert element. A thermal soldering process secures the insert element into the anchoring element. The protruding portion of the insert element and remaining excess solder are removed to form a planar surface.

13 Claims, 1 Drawing Sheet

HYBRID DENTAL IMPLANT AND PRODUCTION METHOD

FIELD OF THE INVENTION

The invention relates to a hybrid dental implant including an endosseus anchoring element made of a ceramic material, and an insert element made of a metal such as a titanium-based metal that is secured, for example by soldering with a glass solder, into a hole provided in a cervical end face of the anchoring element. The invention further relates to a method and a kit of parts for producing such a hybrid dental implant.

BACKGROUND INFORMATION

Two-part dental implants of the above general type, namely hybrid implants wherein the two components are respectively made of different materials, have already become known in various embodiments, for example as disclosed in German Patent Publication DE 10 2011 015 299 A1 and European Patent Publication EP 26 88 510 B1. Furthermore, European Patent Publication EP 27 42 905 A1 discloses a dental implant of a ceramic material having a bored hole for inserting a threaded sleeve of a titanium material, which is then to be secured by soldering with a glass solder. Similarly, European Patent Publication EP 20 39 319 A1 proposes a dental implant consisting of a ceramic material, as well as a separate insert element that is secured by a joining process into a recess of the implant. Further, according to PCT Patent Publication WO 2012/126447 A1, it is known to provide a silicate glass ceramic coating on an outer surface of a dental implant made of a ceramic material, and to apply a layer of titanium thereon.

Such hybrid implant structures including two parts made of different materials, namely the anchoring element of a ceramic material, and the insert element of a titanium material for receiving a prosthetic tooth abutment via a corresponding threading, are advantageous compared to one-piece dental implants, because the two-part hybrid implants avoid or reduce the occurrence of an abrasive wear or a stripped threading or a threading pull-out in the ceramic material of the anchoring element, which tend to occur in practice with one-piece implants of ceramic.

However, on the other hand, with hybrid implants it is difficult to achieve an optimal joint strength and security as well as a gap-free, bubble-free and void-free joint when soldering with a glass solder for connecting the insert element made of a titanium material into the anchoring element made of a ceramic material.

SUMMARY OF THE INVENTION

In view of the above, it is an object of the invention to provide a simple structural embodiment and configuration for a hybrid dental implant, a kit of components to produce such a hybrid dental implant, and a simple method of producing such a hybrid dental implant. A further, more particular object of the invention is to achieve a homogeneous reproducible solder joint and connection with a glass solder between the joining surfaces of the insert element made of a titanium-based material and the anchoring element made of a ceramic material. It is a particular aim of the invention to surely and reliably achieve such a soldered joint without air inclusions, bubbles or voids between the two components of such a hybrid dental implant. The invention further aims to avoid or overcome the disadvantages of the prior art, and to achieve additional advantages, as apparent from the present disclosure. The attainment of these objects is, however, not a required limitation of the claimed invention.

The above objects can be achieved in a dental implant according to an embodiment of the invention, comprising an endosseus anchoring element made of a ceramic material, and an insert element that is made of a titanium-based material and that is received and secured by soldering with a glass solder in a blind hole provided in the anchoring element. Particularly according to this embodiment of the invention, the insert element comprises lateral spacer members at least in the region of the joint to be formed by the glass solder, in order to form and maintain a circumferential gap space around the insert element, i.e. between the insert element and the inner wall of the blind hole in the anchoring element. According to a further preferred feature, the spacer members are not continuous, but rather are shorter than and discontinuous in the circumferential direction and/or the axial or longitudinal direction of the insert element. These discontinuous spacer members can be regarded as having a punctual or point-like configuration that protrude in the form of protruding studs, knobs, bumps, nubs or stumps, or the like radially outwardly from the preferably generally cylindrical outer surface of the main body of the insert element, thereby giving the outer surface of the insert element a punctate configuration.

The above objects can further be achieved by another embodiment of a dental implant according to the invention, wherein the insert element is axially or longitudinally longer than the axial length or depth of the blind hole in the anchoring element, so that when the insert element is inserted and secured in the blind hole, a protruding portion of the insert element protrudes or projects out of the blind hole, outwardly from an end face of the anchoring element. Further according to this embodiment, to carry out the soldering, an excess amount of a glass solder suspension is introduced into the blind hole so that when the insert element is inserted into the blind hole, the excess glass solder suspension is displaced and squeezed out of the blind hole, and forms a protruding excess amount of the solder material adjoining the protruding portion of the insert element on the end face (e.g. the cervical end face) of the implant. After performing a thermal soldering process in a thermal soldering phase under vacuum, the protruding portion of the insert element and the excess amount of solder material on the end face of the anchoring element are preferably separated and removed (e.g. by sawing, grinding, polishing, etc.) to preferably form a flat planar end face of the dental implant.

The above features of the invention achieve advantageous effects as follows. The spacer members on the insert element preferably center the insert element in the blind hole of the anchoring element, and form and maintain a continuous gap space between the insert element and inner wall of the blind hole in the anchoring element, whereby this gap space has a continuous uniform width all around the insert element. This helps to alleviate or avoid critical stresses arising in the glass matrix during the soldering process. The resulting uniform-thickness and continuous glass solder joint layer achieves an improved joining characteristic. Furthermore, the excess amount of the glass solder suspension that is filled into the blind hole and squeezes out to form an excess solder material at the end face of the anchoring element provides a supply reservoir of extra solder material that can be drawn into the joint i.e. the gap space during the soldering process. This helps to prevent the formation of shrinkage voids in the gap space despite the occurrence of shrinkage during the soldering process. Furthermore, the gap space is preferably configured and dimensioned to create a capillary effect that draws the excess solder into the gap space when any shrinkage of the solder material arises during the soldering process. Further preferably, the components are configured and dimensioned so that the capillary effect is concentrated especially in the direction toward the cervical end face of the implant. Still further, the protrusion of the insert element beyond the end face of the anchoring element ensures that the excess solder material cannot flow over the end of the insert element and for example into a threaded receiver hole provided axially in the end of the insert element.

Alternatively, the insert element may initially be formed of solid material (i.e. without the receiver hole). After such a solid insert element is soldered into the blind hole of the anchoring element, then the receiver hole can be bored axially into the end face of the insert element, and then the threading can be tapped into the bored receiver hole. This can improve the precision because the threading is then not subjected to the thermal processing of the soldering step, which could otherwise cause the formation of an oxide layer on a pre-existing threading. In such a case when a previously existing threading becomes oxidized, an acid cleaning step might be necessary. Such additional special cleaning processes are also avoided by tapping the threading into the receiver hole after the soldering process has been completed.

According to a further preferred detailed embodiment feature of the invention, the insert element preferably additionally comprises one or more spacer members on a bottom end portion thereof, for example on an axial end face thereof positioned in the bottom of the blind hole of the anchoring element. These additional spacer members form the gap space and thereby further ensure a good material flow and distribution of the glass solder suspension also between the axial end face of the insert element and the bottom or floor of the blind hole of the anchoring element.

Still further, to achieve a crack-free soldered joint, it is recommended according to a further embodiment feature of the invention, that the width of the gap space shall preferably be not more than 0.5 mm. The gap space width should preferably be maintained uniform and consistent at all locations between the main body of the insert element and the inner wall of the blind hole of the anchoring element.

According to a further preferred embodiment feature of the invention, the outer surface of the insert element is preferably pre-coated with a coating layer of a ceramic primer before being inserted and soldered into the blind hole of the anchoring element. This serves to avoid or cover-over a dark oxide layer of the titanium-based material of the insert element that can arise during the thermal treatment of the soldering process.

The above objects can further be achieved by an embodiment according to the invention for a method of producing such a dental implant. The components of the dental implant may have the features as described above and further herein. The method involves filling the glass solder suspension into the blind hole of the anchoring element, and then inserting the insert element. The amount or quantity of the glass solder suspension introduced into the blind hole is preferably pre-determined (e.g. selected or calculated) so that inserting the insert element displaces and squeezes out an excess amount of the solder suspension after the remaining solder suspension has filled the circumferential gap space between the insert element and the inner wall of the blind hole of the anchoring element. The excess amount of solder suspension rides up and preferably adheres onto and around at least a part of the protrusion portion of the insert element and at least a part of the end face of the anchoring element. Next, a thermal soldering process is carried out under vacuum at a temperature in a range around 800° C. (e.g. +/−20° C., or +/−10° C., or a range from 780° C. or 790° C. up to 800° C.). During the soldering process, as the glass and/or other components in the solder suspension soften and/or melt, the solder suspension tends to shrink or contract. At this time, some of the excess solder suspension at the end face of the anchoring element is drawn into the gap space, for example by a capillary effect, to ensure a complete, uniform, void-free filling of the gap space with the solder material at the completion of the thermal soldering process. After completion of the soldering process, the components are cooled. Then, the protrusion portion of the insert element as well as any remaining excess amount of glass solder protruding beyond the end face of the anchoring element can be removed, for example by sawing, grinding, polishing, etc., to form a planar surface of the end face of the dental implant. Through this method, it is possible to produce a dental implant having the features and advantageous as described herein.

According to a further preferred method embodiment feature of the invention, the outer surface geometry of the insert element is coated in a wetting manner with the glass solder suspension before the insert element is inserted into the blind hole of the anchoring element. This helps to ensure a good adhesion and uniform distribution of the solder material onto the surface of the insert element when it is inserted into the anchoring element.

Furthermore, to achieve a good compaction and good distribution of the introduced glass solder suspension throughout the gap space and onto the adjoining surfaces of the insert element and the anchoring element, the insert element is preferably subjected to vibration when it is in its inserted position in the blind hole of the anchoring element.

It is further suggested according to a preferred embodiment feature of the invention, that the glass solder suspension has a grain size below 15 μm in order to ensure a good flowing of the glass solder suspension in the gap space under pressure and vibration, during the inserting of the insert element and during the thermal soldering process, without the glass solder suspension exhibiting a rheopexy effect of a time-dependent increase in its viscosity as the glass solder suspension is subjected to the shearing forces due to the flowing and vibration.

The above objects can also be achieved by a kit of components for producing such a dental implant, according to a further embodiment of the invention. The components of the kit include the anchoring element, the insert element and the glass solder suspension as disclosed herein.

BRIEF DESCRIPTION OF THE DRAWINGS

In order that the invention may be clearly understood, it will now be explained in further detail in connection with example embodiments thereof, with reference to the accompanying drawings, wherein.

DETAILED DESCRIPTION OF PREFERRED EXAMPLE EMBODIMENTS

Figure 1:
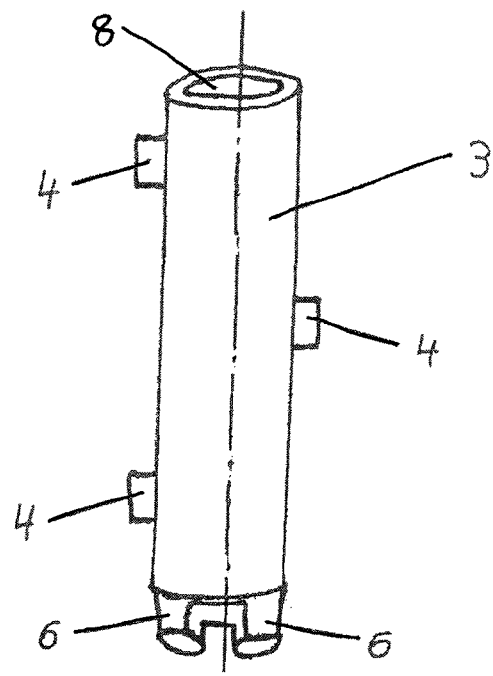
FIG. 1 is a schematic side perspective view of an insert element for a dental implant according to an embodiment of the invention.

As can be seen in FIGS. 1 to 4, a hybrid dental implant according to an embodiment of the invention includes an endosseus anchoring element 1 made of a ceramic material, preferably based on zirconium oxide in this embodiment, and an insert element 3 made of a titanium-based material, e.g. titanium metal or a titanium alloy. The anchoring element 1 has a blind hole 2 introduced axially into an end face, e.g. the cervical end face, of the anchoring element 1. The insert element 3 is to be inserted into the blind hole 2 of the anchoring element 1, and secured in place by a soldered joint formed of a glass solder.

The insert element 3 includes a generally cylindrical insert element body, and lateral spacer members 4 protruding radially outwardly from the cylindrical outer surface of the cylindrical body. In this embodiment, the spacer members 4 are non-continuous and shorter than the cylindrical body in the axial and radial directions of the insert element 3, and thus have generally punctual or point-shaped configurations, e.g. as studs, knobs, bumps, nubs, stumps or protrusions extending in the radial direction, but with limited dimensions in the axial and circumferential directions. The lateral spacer members 4 are configured, dimensioned and located to ensure that the insert element 3 is properly centered within the blind hole 2 of the anchoring element 1, and to ensure that a consistent uniform gap space 5 is formed circumferentially around the insert element 3, between the insert element 3 and the inner wall of the blind hole 2 of the anchoring element 1. For example, in this regard, lateral spacer members 4 are provided at preferably at least three locations uniformly circumferentially spaced around the circumference of the insert element 3, and at least two locations spaced axially from one another in the axial direction of the insert element 3. Additionally in this illustrated embodiment, axial or terminal spacer members 6 are provided protruding axis-parallel from a bottom end face of the body of the insert element 3 to form and maintain a proper gap space relative to the bottom floor of the blind hole 2 of the anchoring element 1. The spacer members are preferably, but not necessarily, formed of the titanium-based material, integrally and monolithically as one piece with the generally cylindrical body of the insert element 3.

As can be seen especially in FIGS. 3 and 4, the insert element 3 in this embodiment has an axial length greater than the axial depth of the blind hole 2 of the anchoring element 1, so that in the inserted condition, a protrusion portion 7 of the insert element 3 protrudes axially from the end face or shoulder 11 of the anchoring element 1, as will be discussed further below.

Figure 2:
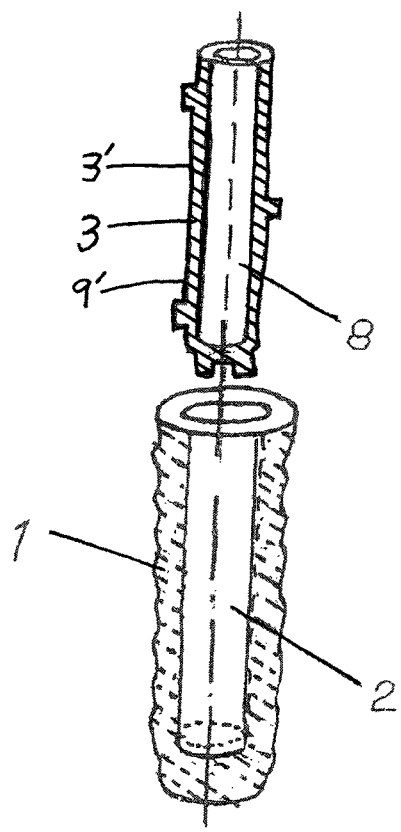
FIG. 2 is a schematic perspective sectional view of the insert element about to be inserted into an associated anchoring element of the dental implant.

The insert element 3 is further provided with a receiver hole 8, which is preferably a threaded receiver hole having an internal screw threading, in order to receive a threaded pin or threaded stud of a prosthetic tooth abutment after the completed hybrid implant has been surgically implanted into the alveolar bone of the mandible or maxilla of a dental patent. For improved osseointegration, the outer surface of the anchoring element 1 may have a threading, ridges, grooves, roughened texture, angular faces, etc. in any known manner and configuration, for example as depicted in FIG. 3. In the present illustrated embodiment, the threaded receiver hole 8 is previously provided in the insert element 3, as can be seen in FIG. 1, before the insert element is inserted and soldered into the anchoring element 1 as shown in FIGS. 2 to 4. Alternatively, the insert element 3 can initially be formed of a solid material without the receiver hole 8. In such an alternative embodiment, the receiver hole 8 is bored axially into the insert element 3 after the insert element 3 has been secured into the anchoring element 1 by completion of the soldering process, for example at the stages shown in FIGS. 3 and 4. Note that FIG. 3 does not show the receiver hole 8, as an example of such an alternative embodiment, and FIG. 4 shows the anchoring element 1 and the glass solder material 9 sectioned on a section plane parallel to the axis of the dental implant, but shows the insert element 3 merely from its outside without sectional illustration thereof. Thus, FIG. 4 applies to both embodiments, namely with and without a previously formed receiver hole 8 in the insert element 3. An internal threading may be tapped into the hole after it has been bored. As a further alternative, the receiver hole 8 may be previously provided as a smooth-bore cylindrical hole in the insert element 3 before inserting and soldering the insert element 3 into the anchoring element 1, but then an internal threading is tapped into the receiver hole 8 after completion of the soldering process, to ensure that the threading is precise, clean and not oxidized.

Figure 3:
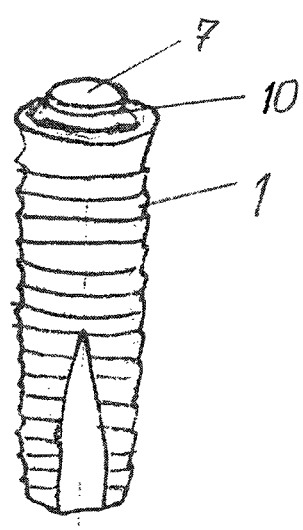
FIG. 3 is a schematic perspective view of the dental implant including the insert element received in the anchoring element, wherein a protrusion of the insert element and excess glass solder material can be seen protruding on the shoulder of the implant.

Before carrying out the thermal soldering process, the blind hole in the anchoring element 1 is partially filled with a predetermined amount of a glass solder suspension 9, and then the insert element 3 is inserted, as represented in the transition from FIG. 2 to FIG. 3. The amount of the glass solder suspension 9 is determined in connection with the dimensions and configuration of the components, so that insertion of the insert element 3 causes a pre-determined excess amount 10 of the glass solder suspension to be displaced and squeezed out of the blind hole 2 after the glass solder suspension has entirely filled the gap space 5 around the insert element 3. The excess amount 10 of solder material is thus disposed on the end face or shoulder 11 of the anchoring element 1 and on the protrusion portion 7 of the insert element 3 protruding beyond the end face 11, as shown in FIGS. 3 and 4. This assembled arrangement is then subjected to the thermal soldering process under vacuum at a temperature in a range up to or around 800° C. After completion of the soldering process and cooling of the soldered arrangement, the remaining excess amount 10 of the solder material and the protrusion portion 7 of the insert element 3 are preferably removed, for example by sawing, grinding, polishing, etc. to form a flat planar end face of the finished dental implant.

An example embodiment of a method for producing the dental implant according to the invention is thus performed essentially by carrying out the following method steps. The outer surface of the insert element 3 is wetted with some of the glass solder suspension to form a coating 9' of the glass solder suspension on the insert element 3. Optionally, a coating 3' of a ceramic primer may also be provided on the outer surface of the insert element 3 before its insertion into the blind hole 2 of the anchoring element 1, to further improve the adhesion of the glass solder material. The blind hole 2 of the anchoring element 1 is partially filled with (preferably a predetermined amount of) the glass solder suspension 9. Then the pre-coated insert element 3 is inserted into the solder-filled blind hole 2 of the anchoring element 1. By its spacer members 4 and 6, the insert element 3 is positioned centered within the blind hole 2 while forming the consistent uniform gap space 5 between the insert element 3 and the anchoring element 1. Vibration is applied to the insert element 3, which in turn imposes vibration onto the glass solder suspension 9, whereby the glass solder suspension is dispersed, uniformly distributed, and compacted. The introduced amount of the glass solder suspension 9 was preferably predetermined such that the insertion and vibration of the insert element 3 causes a pre-defined limited excess amount 10 of the glass solder material to be displaced and squeezed out of the blind hole 2 such that the excess amount 10 of solder is disposed outside of the gap space 5 adjoining on the upper shoulder 11 of the end face of the anchoring element 1 and on the protrusion 7 of the insert element 3. The excess amount 10 of solder material may adhere by a capillary effect and surface tension onto the protrusion 7 of the insert element 3 and the end face of the shoulder 11 of the anchoring element 1 at the open end of the gap space 5. The protrusion 7 of the insert element 3 forms a boundary to limit or contain the flow of the excess solder 10. Thus, the excess solder 10 cannot flow into the receiver hole 8 of the insert element 3. Instead the excess solder 10 is maintained at the upper open end of the gap space 5 in a controlled space so that it provides a supply reservoir of extra solder suspension that can be drawn into the gap space 5 as the solder suspension in the gap space shrinks or contracts during the soldering process.

The soldering process comprises a thermal firing at a temperature in a range up to or around 800° C. under vacuum, whereby the glass solder suspension 9 shrinks or contracts. At that time, solder suspension from the excess amount 10 at the open end of the gap space 5 is drawn into the gap space 5 to become part of the solder joint. This helps to avoid the formation of shrinkage cavities or voids in the finished solder joint. After completion of the thermal firing process, and cooling of the components, the protrusion 7 of the insert element 3 and any remaining excess amount 10 of the solder material is removed, e.g. by sawing, grinding, polishing and the like, so as to form a flat planar surface at this end face of the finished hybrid implant.

Figure 4:
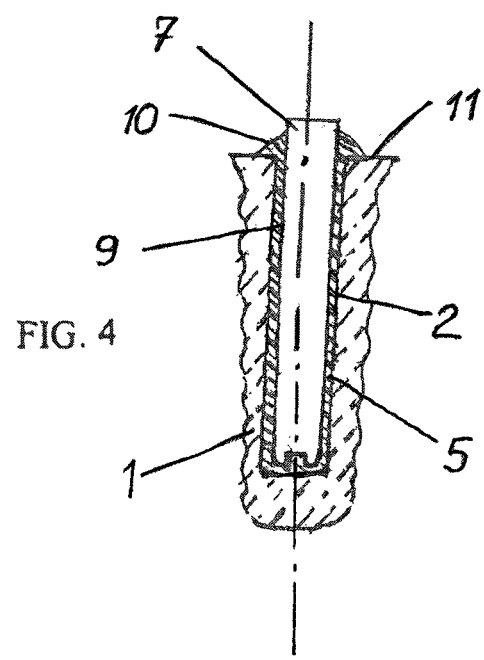
FIG. 4 is a schematic view, partially sectioned, of the assembled dental implant according to FIG. 3.

The dental implant as shown in FIGS. 3 and 4 can be regarded as representing a semi-finished state, after the soldering is completed, but before removal of the protruding portion 7 of the insert element 3 and the remaining excess solder 10 to form a finished dental implant. The illustrated configuration could also be regarded as a finished state of the dental implant. In any event, the illustrated state or condition is still termed a dental implant, e.g. as covered in the appended claims.

The glass solder suspension can refer to any known suspension, slurry or other composition of glass and other ingredients to prepare the starting solder material to be fired to form a soldered glass joint. The term glass solder also covers and can be referred to as a ceramic solder. The term "made of" generally means "comprising", and not strictly "consisting only and entirely of".

Although the invention has been described with reference to specific example embodiments, it will be appreciated that it is intended to cover all modifications and equivalents within the scope of the appended claims. It should also be understood that the present disclosure includes all possible combinations of any individual features recited in any of the appended claims. The abstract of the disclosure does not define or limit the claimed invention, but rather merely abstracts certain features disclosed in the application.

What is claimed is:

1. A dental implant comprising:
   an anchoring element made of a ceramic material, having a blind hole extending into the anchoring element from an end face of the anchoring element, wherein an inner wall surface of the anchoring element bounds the blind hole;
   an insert element comprising an insert element body made of a titanium-based material, wherein the insert element is at least partially received in the blind hole with a circumferentially continuous gap space between the insert element body and the inner wall surface of the anchoring element in the blind hole; and
   a solder joint layer of a glass solder material that is disposed in the gap space, by which the insert element is joined with the anchoring element;
   wherein the insert element further includes lateral spacer members, which protrude laterally outwardly from a lateral surface of the insert element body, and which define and maintain the circumferentially continuous gap space between the insert element body and the inner wall surface of the anchoring element in the blind hole, and
   wherein the lateral spacer members are punctiform spacer members that have a punctual configuration that is shorter than and non-continuous over an axial length and a circumference of the inner wall surface of the blind hole of the anchoring element.

2. The dental implant according to claim 1, wherein the punctual configuration of each one of the lateral spacer members is a configuration selected from studs, knobs, bumps, nubs and stumps.

3. The dental implant according to claim 1, wherein the insert element further comprises at least one terminal spacer member, which protrudes from a terminal end of the insert element body in the blind hole, and which defines and maintains an end gap between the terminal end of the insert element and a blind end wall of the anchoring element bounding a blind end of the blind hole, and wherein the solder joint layer of the glass solder material further extends into the end gap.

4. The dental implant according to claim 1, wherein the insert element has an axial length greater than an axial depth of the blind hole, a protruding portion of the insert element protrudes out of the blind hole outwardly beyond the end face of the anchoring element, and an excess portion of the glass solder material protrudes from the solder joint layer out of the gap space and adjoins at least partially onto the protruding portion of the insert element and the end face of the anchoring element.

5. The dental implant according to claim 1, wherein the ceramic material is a zirconium oxide based ceramic.

6. The dental implant according to claim 1, wherein the insert element has therein an internally threaded receiver hole extending coaxially with an axis of the blind hole of the anchoring element.

7. The dental implant according to claim 1, wherein the dental insert is in a semi-finished state, in which the insert element is a solid body of the titanium-based material without any hole therein extending coaxially with an axis of the blind hole of the anchoring element.

8. The dental implant according to claim 1, wherein the gap space has a width of at most 0.5 mm.

9. The dental implant according to claim 1, wherein the insert element further comprises an outer coating of a ceramic primer.

10. A kit of components for producing a dental implant, comprising:

an anchoring element made of a ceramic material, having a blind hole extending into the anchoring element from an end face of the anchoring element, wherein an inner wall surface of the anchoring element bounds the blind hole;

an insert element comprising an insert element body made of a titanium-based material, and lateral spacer members that protrude laterally outwardly from a lateral surface of the insert element body, wherein the insert element has an axial length greater than an axial depth of the blind hole, wherein the insert element is configured and dimensioned to be inserted into the blind hole of the anchoring element whereby the lateral spacer members define and maintain a circumferentially continuous radial gap space between the insert element body and the inner wall surface of the anchoring element in the blind hole and whereby a protruding portion of the insert element protrudes out of the blind hole outwardly beyond the end face of the anchoring element and wherein the lateral spacer members are punctiform spacer members that have a punctual configuration that is shorter than and non-continuous over an axial length and a circumference of the inner wall surface of the blind hole of the anchoring element; and a glass solder suspension in an amount greater than a volume of the gap space so that when the glass solder suspension and the insert element are introduced into the blind hole then an excess portion of the glass solder suspension is displaced out of the blind hole and adjoins at least partially onto the protruding portion of the insert element and the end face of the anchoring element.

11. The dental implant according to claim 1, wherein the spacer members are arranged and configured to radially center the insert element in the blind hole of the anchoring element.

12. The dental implant according to claim 1, wherein the gap space and the solder joint layer disposed in the gap space each respectively extend continuously and entirely along the axial length and the circumference of the inner wall surface of the blind hole of the anchoring element interrupted only by the punctiform spacer members.

13. The dental implant according to claim 1, wherein the gap space has a continuous uniform radial gap width extending around an entire circumference of the insert element body.

* * * * *